United States Patent
Kettunen et al.

(10) Patent No.: US 10,040,744 B2
(45) Date of Patent: Aug. 7, 2018

(54) METHOD FOR KETONISATION OF BIOLOGICAL MATERIAL

(71) Applicant: NESTE OYJ, Espoo (FI)

(72) Inventors: Mika Kettunen, Helsinki (FI); Jukka Myllyoja, Vantaa (FI); Rami Piilola, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/521,134

(22) PCT Filed: Oct. 23, 2015

(86) PCT No.: PCT/EP2015/074622
§ 371 (c)(1),
(2) Date: Apr. 21, 2017

(87) PCT Pub. No.: WO2016/062868
PCT Pub. Date: Apr. 28, 2016

(65) Prior Publication Data
US 2017/0362154 A1    Dec. 21, 2017

(30) Foreign Application Priority Data

Oct. 24, 2014 (EP) .................................. 14190302

(51) Int. Cl.

| | |
|---|---|
| *C07C 45/48* | (2006.01) |
| *B01J 23/00* | (2006.01) |
| *C10G 3/00* | (2006.01) |
| *C10G 45/58* | (2006.01) |
| *B01J 23/04* | (2006.01) |
| *B01J 23/883* | (2006.01) |

(52) U.S. Cl.
CPC ............... *C07C 45/48* (2013.01); *B01J 23/04* (2013.01); *B01J 23/883* (2013.01); *C10G 3/46* (2013.01); *C10G 3/50* (2013.01); *C10G 45/58* (2013.01); *C10G 2300/1011* (2013.01); *C10G 2400/10* (2013.01)

(58) Field of Classification Search
CPC .................. C07C 45/48; B01J 23/04
USPC .......................................................... 568/397
See application file for complete search history.

(56) References Cited

U.S. PATENT DOCUMENTS

| | | |
|---|---|---|
| 4,950,763 A | 8/1990 | Schommer et al. |
| 4,950,765 A | 8/1990 | Walsgrove et al. |
| 2009/0014354 A1 | 1/2009 | Knuuttila et al. |
| 2015/0018581 A1 | 1/2015 | Kettunen et al. |
| 2015/0018588 A1 | 1/2015 | Myllyoja et al. |
| 2015/0251168 A1 | 9/2015 | Kettunen et al. |

FOREIGN PATENT DOCUMENTS

| | | |
|---|---|---|
| WO | WO 2007/068795 A1 | 6/2007 |
| WO | WO 2007/068797 A2 | 6/2007 |
| WO | WO 2007/068797 A3 | 6/2007 |
| WO | WO 2013/113976 A1 | 8/2013 |
| WO | WO 2013/113977 A1 | 8/2013 |

OTHER PUBLICATIONS

International Search Report (PCT/ISA/210) dated Nov. 20, 2015, by the Japanese Patent Office as the International Searching Authority for International Application No. PCT/EP2015/074622.
Written Opinion (PCT/ISA/237) dated Nov. 20, 2015, by the Japanese Patent Office as the International Searching Authority for International Application No. PCT/EP2015/074622.
Written Opinion dated Jan. 23, 2018, by the Intellectual Property Office of Singapore in corresponding Singaporean Application No. 11201703178Y. (6 pages).

*Primary Examiner* — Sikarl A Witherspoon
(74) *Attorney, Agent, or Firm* — Buchanan Ingersoll & Rooney, PC

(57) ABSTRACT

A method for producing ketones includes a) providing a feedstock of biological origin having fatty acids and/or fatty acid derivatives having an average chain length of 24 C-atoms or less; b) subjecting the feedstock to a catalytic ketonization reaction in the presence of a $K_2O/TiO_2$-catalyst; and c) obtaining from the ketonization reaction a product stream having ketones, which ketones have a longer average hydrocarbon chain length than the average hydrocarbon chain length in the feedstock, wherein step b) is carried out directly on the feedstock and in the presence of the $K_2O/TiO_2$-catalyst as the sole catalyst applied in the ketonization reaction.

20 Claims, 2 Drawing Sheets

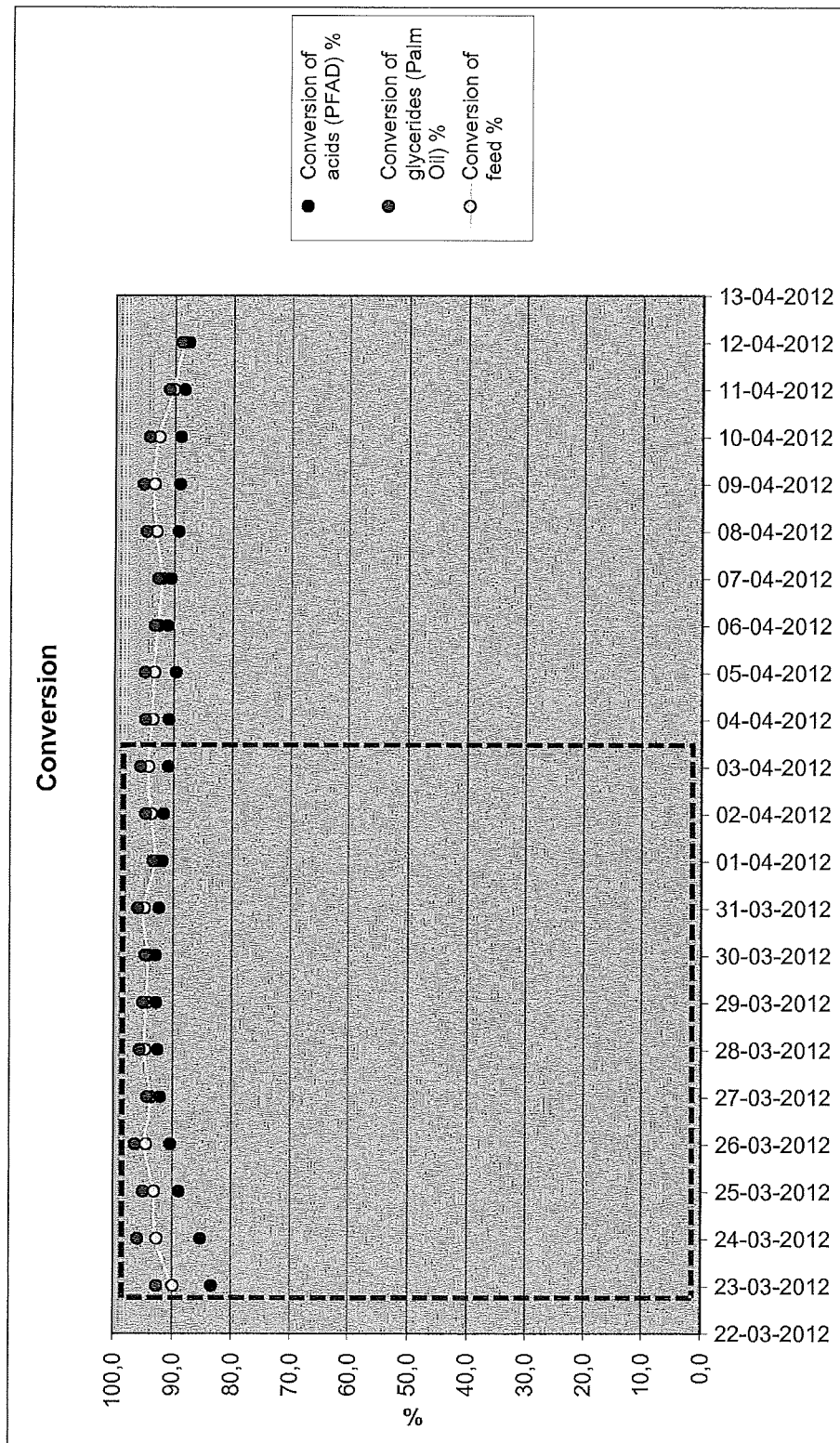
Figure 2. Ketonisation with 100% KEC-25 catalyst; conversion of feed. Red dotted area represents days that were combined to feed to hydrogenation proces

METHOD FOR KETONISATION OF BIOLOGICAL MATERIAL

TECHNICAL FIELD

The present invention relates to a method of producing ketones in a new catalytic method and the use of such ketones.

BACKGROUND ART

Production of hydrocarbons used as fuel, heavy oil and base oil components and chemicals from biomass are of increasing interests since they are produced from a sustainable source of organic compounds.

Base oils find use for modern engine lubrication technologies. A high-quality base oil should enable engines to deliver high-level performance and power without compromising fuel economy or environmental standards, and there is a need for renewable sources in the production of base oils and lubricants. Oils from biomass contain free fatty acids and triglycerides; however, the hydrocarbons chain lengths in the fatty acids are too short for base oils with the qualities wished for. Ketonization, by combining two fatty acids to form a long chain ketone is an appropriate reaction route for formation of suitable long-chained hydrocarbons applicable as base oil components. The long chain ketones can readily be hydrogenated to yield straight chain hydrocarbons. The hydrocarbons in turn can be further isomerized to produce various base oil components.

WO2013/113976 describes a method for simultaneous production of fuel components and base oil components from renewable feedstock by reaction of a feedstock comprising free fatty acids and/or fatty acids esters in a reaction zone in the presence of a dual catalyst system. The dual catalyst system described in the publication is configured to perform a ketonization reaction and a hydro treatment reaction. The aim of the method described is to produce a mixture of base oil components (>C24 hydrocarbons chains) and fuel oil components (C11-C23 hydrocarbon chains).

WO2007/068795 describes both a base oil component, produced from biological material, and a method for producing base oil components from biological material. The described method comprises a ketonization step, followed by a hydrodeoxygenation step and an isomerization step. By this method all the biological material, fatty acids and triglycerides, are hydrolysed and saturated before subjecting the feedstock to the ketonization step. Besides, the ketonization step must be performed in gas phase. This method therefore requires several additional steps and harsh conditions.

Publication WO2013/113977 describes a method for increasing the length of the hydrocarbon chain in the fatty acids by subjecting fatty acids and/or fatty acid esters with a hydrocarbon chain length below C23 to a ketonization step in the presence of a hydrotreatment catalyst under hydrogen pressure. The catalyst used in the publication is a typical desulphurization catalyst, namely a supported NiMo catalyst.

There is still a need for a more robust and simpler method of producing base oil components from biological material. The method should require only a few steps and relatively mild conditions, be easy to control and produce a high yield, in order to be economically and technologically feasible.

SUMMARY OF INVENTION

The present invention was made in view of the prior art described above, and the main object of the present invention is to provide a method that it is simple, cost-effective and straight-forward for increasing the chain length of hydrocarbons of biological origin through ketonization of naturally occurring fatty acids, so that the ketones are suitable for use as base oil components or as intermediate material for base oil components. The carbon chain lengths of naturally occurring fatty acids are in the range of C12 to C24, which is suitable e.g. in diesel fuel. However, base oil components typically have a carbon chain length of C24 to C48.

Another object is to provide a method that can be performed on a feedstock of triglycerides or a mixture of triglycerides and free fatty acids, as well as on fatty acid derivatives such as fatty acid esters, including mono-, di and triglycerides.

Yet another object is to provide a ketonization method which can also be performed directly on unsaturated fatty acids, without the need of hydrogenating the double bonds of the naturally occurring fatty acids.

Furthermore, an object of the invention is to provide a ketonization method that can be performed on a liquid feedstock, without the need of gasification of the feedstock, and which is easy to control.

These objects are achieved by using a K2O/TiO2 ketonization catalyst.

Accordingly, the present invention provides in a first aspect a method for producing ketones, the method comprising the steps of:
  a) providing a feedstock of biological origin comprising fatty acids and/or fatty acid derivatives having an average chain length of 24 C-atoms or less,
  a) subjecting said feedstock to a catalytic ketonization reaction in the presence of a $K_2O/TiO_2$-catalyst,
  b) obtaining from said ketonization reaction a product stream comprising ketones, which ketones have a longer average hydrocarbon chain length compared to the average hydrocarbon chain length of said feedstock,
wherein step b) is carried out directly on said feedstock and in the presence of said $K_2O/TiO_2$-catalyst as the sole catalyst applied in said ketonization reaction.

Surprisingly, the present inventors have found that the ketonization reaction can be effected simply by using the $K_2O/TiO_2$-catalyst and can be performed directly on the feedstock of biological origin comprising triglycerides or a mixture of triglycerides and free fatty acids, including unsaturated fatty acids, as well as fatty acid derivatives such as esters, including mono-, di- and triglycerides, and without hydrogenation of the double bonds that are present in naturally occurring fatty acid products in various amounts.

It is also surprising that the present ketonization method that can be performed by introducing the feedstock in liquid phase, without the need of gas phase introduction of the feedstock. Fatty acids and especially esters of fatty acids, such as triglycerides, have high boiling points and gasification of the fatty acids, if required, would require lots of energy. However, the present ketonization method does not require gasification and therefore can be carried out in a smaller reactor, compared to gas phase ketonization. The method can also be used on a broader selection of feedstock material comprising mostly unsaturated fatty acids in the triglycerides, because the ketonization can be carried out directly without pre-hydrogenation.

According to the present invention the ketonization reaction takes place directly on the feedstock. The degree of ketonization is very high and may typically be 50% or more, sometimes 65% or more, or 75% or more, or even 90% or more. The product of the ketonization reaction is led to a first liquid/gas separator, which separates the ketonization product in the liquid product stream comprising the ketones from the gas.

All these factors contribute to the present method being more simple and cost effective.

Definitions

By "base oil" is meant oil products which can be used as lubricant components.

By "ketonization reaction" is meant the formation of a ketone through a chemical reaction of two compounds, in particular by reaction between the acyl groups in two fatty acids.

By "feedstock" is meant raw material of biological origin; this is further explained in the detailed description of the invention.

By "hydrotreatment" is typically meant a catalytic method which removes oxygen from organic oxygen compounds (hydrodeoxygenation, HDO); sulfur from organic sulfur compounds (hydrodesulfurization, HDS); nitrogen from organic nitrogen compounds (hydrodenitrogenation, HDN); and halogens such as chlorine from organic chloride compounds (dehydrochlorination, HDCl), as well as saturation of carbon-carbon double bonds under a hydrogen pressure.

By "partial hydrotreatment" is meant a hydrotreatment reaction which removes oxygen, sulphur, nitrogen or halogens only partially, part of the organic compounds will remain.

By "deoxygenation" is meant the removal of covalently bound oxygen from organic molecules.

By "hydrocracking" is meant catalytic decomposition of organic hydrocarbon materials under hydrogen pressure.

By "hydrogenation" is meant saturation of carbon-carbon double bonds by means of molecular hydrogen under the influence of a catalyst.

By "isoparaffin" is meant an alkane having one or more side chains.

By "purification of feedstock" is understood removal of impurities, such as metals and phosphorus.

Viscosity index is a measure of base oil which tells how much the viscosity of base oil changes with temperature. The higher value means better base oil which can maintain its viscosity better at a broader temperature range. Good quality base oil has low enough viscosity for running at cold temperature and is still viscous enough at high temperature.

The invention also provides use of the ketones obtainable by the process of the present invention as base oil components or as intermediates for production of base oil components.

BRIEF DESCRIPTION OF DRAWINGS

In FIG. 1 the ketonization reaction zone is called KETO. The following zones are optional zones for aftertreatment called HDO and ISOM, respectively.

FIG. 2 shows a scheme illustrating the conversion grade after ketonization of feedstocks with a 100% $K_2O/TiO_2$-catalyst.

DETAILED DESCRIPTION OF THE INVENTION

Figure 1:
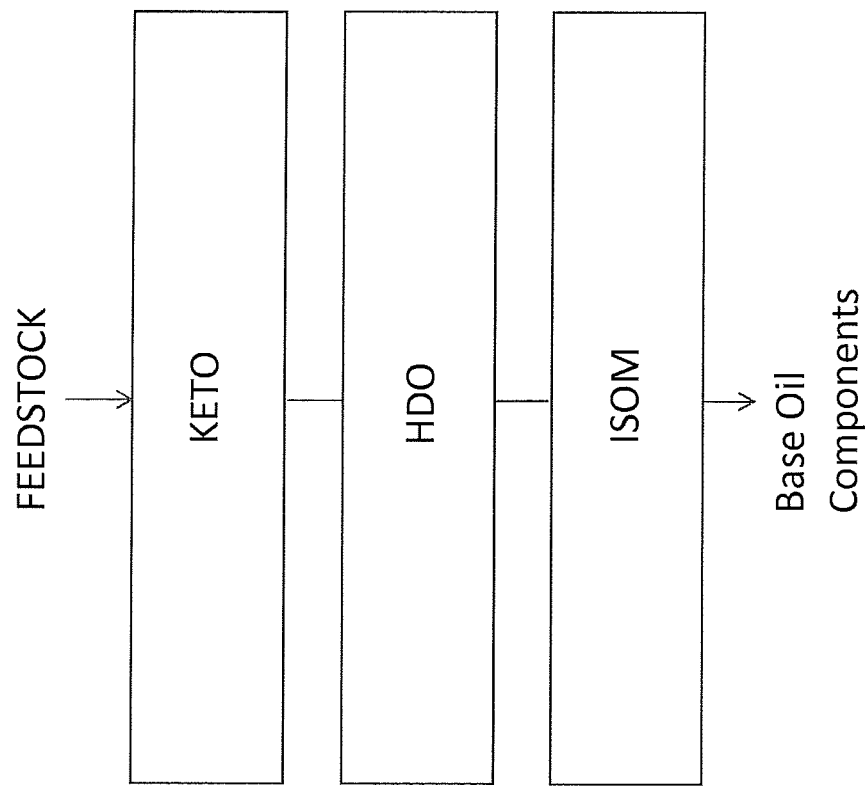
FIG. 1 shows a scheme illustrating the method of the invention.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose. Furthermore, the embodiments described in the following can be combined and mixed to other suitable embodiments.

In a first embodiment of the method of the invention said ketonization reaction is performed by introducing the feedstock in liquid phase. One advantage of this is that the ketonization method requires smaller reactor size compared to gas phase ketonization.

In a second embodiment the feedstock of biological origin, including the triglycerides, comprise unsaturated fatty acids and/or fatty acid derivatives, such as esters.

Feedstock

Typical basic structural unit of plant and fish oils and animal fats is triglyceride. Triglyceride is an ester of glycerol with three fatty acid molecules having the general structure of formula 1 below:

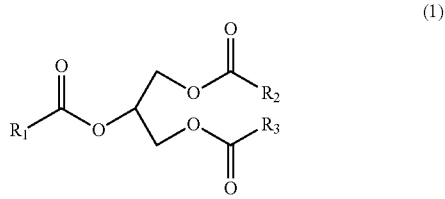

(1)

wherein R1, R2 and R3 represent C4-C26 hydrocarbon chains. The length of the hydrocarbon chain is typically 18 carbons (C18). C18 fatty acids (FA's) are typically bonded to the middle hydroxyl group of glycerol. Typical carbon numbers of the fatty acids linked to the two other hydroxyl groups are even, are generally between carbon numbers C14 and C22. Free fatty acids (FFA's) may be produced industrially by fat splitting or hydrolysis of triglycerides (TC's), with the removal of glycerol. Vegetable oils also comprise free fatty acids.

The feedstock used in the present invention may comprise fatty acids and/or fatty acid esters originating from renewable sources, such as vegetable oils, plant oils, fish oils, animal fats, algae and oils obtained from native or GMO microbes, such as yeast and mould. In particular, the fatty acid esters may comprise triglycerides, such as those of formula 1, and in particular the fatty acid and fatty acid esters may have a high degree of unsaturation. For example, the feedstock may comprise about 70% triglycerides and about 30% free fatty acids, but the amount of free fatty acids may be up to 100% in some embodiments The method of the present invention is perfectly well suited for a feedstock containing a mixture of triglycerides and free fatty acids including unsaturated fatty acids. Typically, commercially available feedstock comprises free fatty acids and/or triglycerides. The method of the present invention is capable of utilising these commercially available feedstocks with good yield without pre-treatment in the form of pre-hydrogenation to saturate the fatty acids and their esters. This simplifies the ketonization reaction in comparison with prior art methods.

For example, triglycerides of palm oil comprises about 45% by weight of saturated fatty acids, about 42% by weight of monounsaturated fatty acids and about 8% by weight of polyunsaturated fatty acids. In one embodiment the feedstock used in the present invention comprises palm oil or palm oil fatty acid, in another embodiment the feedstock is a mixture of palm oil fatty acid from 20 to 40% by weight and palm oil triglycerides from 60 to 80% by weight. In yet another embodiment the feedstock of the present invention comprises palm oil and stearic acid, i.e. a mixture of stearic acid from 20 to 40% by weight and palm oil triglycerides from 60 to 80% by weight.

Decomposition of triglycerides and fatty acid derivatives forms more free fatty acids or other oxygenates which can further undergo ketonization reaction and produce more base oil components and molecules.

The feedstock may be purified before entering it into the processing unit. Decrease of the metal and phosphorus content of the feedstock using the commonly known and available purification methods, including but not limited to bleaching, deodorization and degumming, is advantageous.

Pre-treatments, such as saturation of unsaturated components or reacting or removing triglycerides from biological oils, are not necessary according to the method of the present invention, but can of course be included.

As stated above, the feedstock can be at least partly, and sometimes completely, in liquid form when entered into the ketonization step i.e. to the reaction zone wherein ketonization takes place. Thus, separate vaporization of the fatty acids is not necessary and the use of large amounts of carrier gas can be avoided.

Catalytic Ketonization

The catalytic ketonization reaction is carried out by introduction of the feedstock comprising fatty acids and/or fatty acid derivatives, and optionally product recycle, into a reaction zone. Ketones are formed therein through a ketonization reaction between said fatty acids and/or fatty acid esters, or their reaction products or derivatives, in particular between esters. The feedstock is entered into the reaction zone KETO (FIG. 1) and subjected to ketonization. Gas pressure may be applied, but is not mandatory.

If gas pressure is applied it will effect breaching of the triglycerides and saturation of double bonds in the unsaturated fatty acids and their derivatives; in this embodiment the gas pressure may be such as from 0.5 MPa to 5 MPa, e.g. 1-3 MPa, or e.g. 1.5-2 MPa.

The gas pressure may be achieved by hydrogen or nitrogen or any other suitable gas.

The ketonization reaction applied in the method of the invention is carried out using the $K_2O/TiO_2$-catalyst, which can be supported, e.g. on alumina, silica or active carbon, as the sole catalyst.

According to the present invention a ketonization reaction takes place directly on the feedstock. The degree of ketonization is very high and may typically be 50% or more, sometimes 65% or more, or 75% or more, or even 90% or more. The product of the ketonization reaction is led to a liquid/gas separator, which separates the ketonization product in the liquid product stream comprising the ketones from the gas.

During the ketonization of fatty acids, at least $H_2O$, $CO_2$ and CO gases are released and removed from the oil products.

In one embodiment of the present method the $K_2O/TiO_2$-catalyst is the sole catalyst applied. This embodiment is particular cost-effective and therefore sometimes preferred.

In one embodiment the ketonization reaction is performed in a temperature ranging from 150° C. to 400° C., such as 200° C. to 375° C., e.g. 250° C. to 350° C. or 275° C. to 325° C.; and/or the liquid feed flow rate WHSV is from 0.1 to 10 $h^{-1}$, such as 0.2 to 5 $h^{-1}$, e.g. 0.5 to 1 $h^{-1}$.

The present ketonization reaction provides ketones which in one embodiment of the method of the invention may be further treated by deoxygenation and/or isomerization in single or multiple steps.

Hydrodeoxygenation Step

In one embodiment of the invention the method further comprise a step of hydrodeoxygenation step (HDO), in which the obtained product stream comprising ketones are hydrodeoxygenated to obtain hydrocarbons and for removal of any oxygen traces. The product of the final hydrodeoxygenation step is n-paraffins in diesel range (C11-C23) and in the base oil range (C24-C43). The HDO step may be carried out in accordance with the method disclosed in prior art, e.g. WO2007/068795.

This HDO step may be carried out under a hydrogen gas partial pressure ranging from 0.1 to 20 MPa, such as from 1 and 15 MPa, e.g. from 2 to 10 MPa. The temperature ranges preferably from 100 to 500° C., such as from 150 to 400° C., e.g. from 200 to 350° C. The liquid feed flow rate, WHSV, can e.g. be varied from 0.1 to 10 $h^{-1}$, such as from 1 to 5 $h^{-1}$, e.g. from 1 to 3 $h^{-1}$. In this HDO step, catalysts containing a hydrogenation metal on a support are normally used; the HDO catalyst is e.g. a supported Pd, Pt, Ni, NiMo, NiW or CoMo catalyst, the support being activated carbon, alumina and/or silica.

The product obtained after the HDO step is sometimes purified for instance by stripping with steam or with a suitable gas, such as a light hydrocarbons, nitrogen or hydrogen. It is advantageous to remove impurities (i.e. $H_2S$, $NH_3$, $H_2O$, $CO_2$, CO) as efficiently as possible prior to isomerization step and/or finishing steps.

Isomerisation Step

An Isomerisation step may also be included as aftertreatment in order to improve cold flow properties. By this treatment diesel (C10-C23) and base oil (C24-C43) components from the hydrodeoxygenation step is isomerized together to give isoparaffins. Hydroisomerization of diesel paraffins is known and is typically performed in accordance with the method of prior art, e.g. WO2007/068795, using noble metal bifunctional catalysts, such as Pt-SAPO or Pt-ZSM-catalysts, at a reaction temperature of 300-400° C., pressure of 2-5 MPa and liquid feed flow rate of from 0.5 to 2 $h^{-1}$ with hydrogen. Isomerization of n-paraffins does not as such need hydrogen, but it is important that olefins formed from cracking (side reaction) are quickly hydrogenated. Without the fast olefin saturation, coking of catalyst is observed.

From the ketonization reaction straight chain ketones are formed which give rise to straight chain paraffins (alkanes) when hydrodeoxygenated in the additional step. Isomerisation then provides some branched alkanes and gives good viscosity index and cold flow properties. Oligomerisation reaction of unsaturated fatty acids followed by hydrodeoxygenation gives rise to highly branched paraffins, even cyclic molecules are formed, which are not equally good as base oil components.

In addition, the processing may include several other steps such as distillations steps, e.g. under atmosphere or in vacuum, before or after the isomerisation step.

The hydrodeoxygenation step and the optional isomerization steps can be carried out in the same reaction zone as the ketonization reaction or in separate reaction zone(s) subsequent to the ketonization reaction zone.

Accordingly, in one embodiment of the method of the invention the liquid product stream from the ketonization reaction separated in a first separator is led to the hydrodeoxygenation reaction zone, HDO (FIG. 1), and thereafter the product stream from the HDO reaction zone is led to a second liquid/gas separator which again separates the hydrodeoxygenated product in a liquid product stream comprising ketones from a gas product stream.

The liquid product from the HDO reaction zone can again be led to the isomerisation reaction zone, ISOM (FIG. 1) and the product stream from that reaction zone led to a third liquid/gas separator which again separates the hydrodeoxygenated product into a liquid and a gas product stream.

EXAMPLES

The examples show that it is possible to obtain a very high degree of ketonization, typically 50% or more.

Example 1

A mixture of 70% palm oil (RPO PO) and 30% palm oil fatty acid distillate (PFAD) was subjected to ketonization in the presence of $K_2O/TiO_2$ catalyst. The reaction was carried out using hydrogen to hydrocarbon ($H_2$/HC) ratio of 500 Nl/l (normalized liter per liter) and a weight hourly space velocity (WHSV) of 1.0 $h^{-1}$. The temperature in the KETO unit (FIG. 1) was 365° C., and the pressure was 2 mPa.

After ketonization the product stream was led to a liquid/gas separator wherein the gas stream was separated from the liquid product stream comprising the ketones; 89% was ketone product, and 11% was gas product.

The content of ketones having a hydrocarbon chain length of more than 24 was 58.1%.

Table 1 shows the process conditions and the characteristics of the two product streams.

TABLE 1

Process conditions and product distribution in the ketonisation test

| KETONISATION | | Liquid sample analysis Test | Total mass balance |
|---|---|---|---|
| | | 120323-120403 | 120323-120403 Feed |
| | | PO (70%) PFAD (30%) | PO (70%) PFAD (30%) |
| Temp | ° C. | 366 | 366 |
| Pressure | bar | 22 | 22 |
| WHSV | $h^{-1}$ | 1.0 | 1.0 |
| H:HC | l/l | 512 | 512 |
| $H_2O$ (from liquid separation) | % | | 2 |
| GAS (Liquid yield − 100) | % | | 8.8 |
| $C_{4-10}$ (GC-AREA) | % | 0.3 | 0.3 |
| $C_{11-23}$ (GC-AREA) | % | 41.6 | 37.1 |
| >$C_{24}$ (GC-AREA) | % | 58.1 | 51.7 |
| Sum | % | 100 | 100 |

The conversion degree of components in the feedstock, viz. the fatty acids in the PFAD and the glycerides in palm oil, was 90.5% and 95%, respectively.

The experiment was repeated with further batches with the same feedstock and under similar reaction conditions, resulting in a ketone product stream of 88-91%.

The conversion grade after ketonization of the feedstock with a 100% $K_2O/TiO_2$-catalyst is shown in FIG. 2. Three components of the feedstock are illustrated:
Conversion of acids, (PFAD) in %, which varies from 83.4 to 93.0% in the experiments;
Conversion of glycerides (palm oil) in %, which varies from 92.8 to 96.5% in the experiments; and
Conversion of feed in %, which varies from 90.0 to 95.0% in the experiments.

Example 2

The liquid ketone product stream obtained in example 1 was subjected to hydrodeoxygenation in the presence of a NiMo catalyst. The reaction was carried out using hydrogen to hydrocarbon ($H_2$/HC) ratio of 1000 Nl/l and a weight hourly space velocity (WHSV) of 1.0 $h^{-1}$. The temperature in the HDO unit (FIG. 1) was 310° C., and the pressure was 5 mPa.

After hydrodeoxygenation the product stream was led to a liquid/gas separator, wherein the gas stream along with water was separated from the liquid product stream comprising the ketone derived paraffins (mainly C31, C33 and C35 hydrocarbons). The content of paraffins having an average hydrocarbon chain length of 24 or more was 59%, calculated from the starting material and 69% calculated from obtained liquid hydrocarbons.

Table 2 shows the process conditions and the characteristics of the product stream.

TABLE 2

Process conditions and product distribution in the hydrodeoxygenation test

| HYDROGENATION | | Liquid sample analysis Test Feed | Total mass balance |
|---|---|---|---|
| | | 120323-120403 | 120323-120403 |
| Temp | ° C. | 311 | 311 |
| Pressure | bar | 40 | 40 |
| WHSV | $h^{-1}$ | 1.1 | 1.1 |
| H:HC | l/l | 928 | 928 |
| H2O (from liquid separation) | % | | 3 |
| GAS (Liquid yield − 100) | % | | 1 |
| C4-10 (GC-AREA) | % | 1 | 1 |
| C11-23 (GC-AREA) | % | 30 | 29 |
| C24-36 (GC-AREA) | % | 63 | 60 |
| >C37 (GC-AREA) | % | 6 | 6 |
| Sum | % | 100 | 100 |

Example 3

The liquid waxy hydrocarbon product stream obtained in example 2 was further subjected to isomerisation in the presence of a wax isomerisation catalyst. The reaction was carried out using hydrogen to hydrocarbon ($H_2$/HC) ratio of 800 Nl/l and a weight hourly space velocity (WHSV) of 1.0 $h^{-1}$. The temperature in the ISOM unit (FIG. 1) was 312° C., and the pressure was 5 mPa.

After the isomerisation step the product stream was led to a liquid/gas separator, wherein the gas stream was separated from the liquid product stream comprising the base oil components. The content of base oil having an average hydrocarbon chain length of 24 or more was 47%, calculated from starting material and 56% calculated from the obtained liquid hydrocarbons.

Example 4

The isomerized liquid hydrocarbon product obtained in example 3 was further distillated under atmospheric pressure and a cut point of 280° C. followed by distillation under vacuum and a cut point of 380° C. By the first step of this after-treatment kerosene is removed (18%), and 65% of the original feed stock from the liquid product stream is led to a vacuum distillation zone. In this zone diesel is removed (19%), and 46% of the original feed stock (starting material) was ketone derived base oil product.

The products were analysed as explained in table 3. The viscosity index of the base oil was 158; which indicates that the base oil is of excellent quality.

TABLE 3

Base oil components in the liquid product obtained in example 4:

| | | |
|---|---|---|
| Cloud point | ° C. | −12 |
| Pour point | ° C. | −23 |
| Viscosity 40° C. | mm²/s | 29.0 |
| Viscosity 100° C. | mm²/s | 6.0 |
| Viscosity Index (ASTMD2270) | | 158 |
| GC-Noack volatiles | w/w % | 7 |
| SimDist SP | ° C. | 334 |
| 5 | ° C. | 379 |
| 10 | ° C. | 402 |
| 30 | ° C. | 447 |
| 50 | ° C. | 463 |
| 70 | ° C. | 480 |
| 90 | ° C. | 572 |
| 95 EP | ° C. | 615 |

The invention claimed is:

1. A method for producing ketones, which method comprises:
   a) providing a feedstock of biological origin containing fatty acids and/or fatty acid derivatives having an average chain length of 24 C-atoms or less;
   b) subjecting said feedstock to a catalytic ketonisation reaction in a presence of a $K_2O/TiO_2$-catalyst; and
   c) obtaining from said ketonisation reaction a product stream containing ketones, which ketones have a longer average hydrocarbon chain length than an average hydrocarbon chain length in said feedstock;
   wherein the catalytic ketonisation reaction in step b) is carried out directly on said feedstock and in a presence of said $K_2O/TiO_2$-catalyst as a sole catalyst applied during said ketonisation reaction.

2. The method according to claim 1 wherein the catalytic ketonisation reaction in step b) is carried out directly on said feedstock without preceeding or simultaneous hydrogenation of double bonds present in the fatty acids and/or fatty acid derivatives in said feedstock.

3. The method according to claim 1 comprising:
   performing said ketonisation reaction by introducing the feedstock in liquid phase.

4. The method according to claim 1 wherein said feedstock of biological origin contains unsaturated fatty acids and/or fatty acid derivatives, or esters.

5. The method according to claim 1 comprising:
   performing said ketonisation reaction under a gas pressure of less than 0.5 MPa.

6. The method according to claim 1, comprising:
   performing said ketonisation reaction under gas pressure of from 0.5 MPa to 5 MPa.

7. The method according to claim 5 comprising:
   achieving said gas pressure by hydrogen or nitrogen or any other suitable gas.

8. The method according to claim 1 wherein said $K_2O/TiO_2$-catalyst is supported on alumina, silica or active carbon.

9. The method according to claim 1 comprising:
   performing said ketonisation reaction in a temperature ranging from 150° C. to 400° C., and/or the liquid feed flow rate WHSV is from 0.1 to 10 $h^{-1}$.

10. The method according to claim 1, comprising:
    d) a hydrodeoxygenation step wherein said ketones obtained from said ketonisation reaction are hydrodeoxygenated;
    e) an optional isomerisation step; and
    f) optional step(s) of further after-treatment.

11. The method according to claim 10, comprising:
    carrying out said hydrodeoxygenation step in a presence of a Pd, Pt, Ni, NiMo, NiW or CoMo catalyst optionally being supported, on alumina, silica or active carbon.

12. The method according to claim 10 comprising:
    carrying out said optional isomerisation step in the presence of a Pd, Pt or Ni metal catalyst, or a Pt-SAPO or Pt-ZSM catalyst.

13. The method according to claim 10 comprising:
    carrying out said hydrodeoxygenation step and said optional isomerisation step in the same reaction zone as said ketonisation reaction or in separate reaction zone(s) subsequent to said ketonisation reaction zone.

14. The method of claim 1, comprising:
    including said ketones as base oil components or as intermediate material for product of base oil components.

15. The method according to claim 14, comprising:
    obtaining the ketones from a feedstock containing triglycerides.

16. The method according to claim 1, wherein comprising:
    performing said ketonisation reaction under gas pressure of from 1 MPa to 3 MPa.

17. The method according to claim 1, comprising:
    performing said ketonisation reaction under gas pressure of from 1.5 MPa to 2 MPa.

18. The method according to claim 1 comprising:
    performing said ketonisation reaction in a temperature ranging from 200° C. to 375° C., and/or the liquid feed flow rate WHSV is from 0.2 to 5 $h^{-1}$.

19. The method according to claim 1 comprising:
    performing said ketonisation reaction in a temperature ranging from 250° C. to 350° C., and/or the liquid feed flow rate WHSV is from 0.5 to 1 $h^{-1}$.

20. The method according to claim 1 comprising:
    performing said ketonisation reaction in a temperature ranging from 275° C. to 325° C., and/or the liquid feed flow rate WHSV is from 0.5 to 1 $h^{-1}$.

* * * * *